(12) United States Patent
Pappone et al.

(10) Patent No.: US 10,952,793 B2
(45) Date of Patent: Mar. 23, 2021

(54) METHOD AND SYSTEM FOR ELIMINATING A BROAD RANGE OF CARDIAC CONDITIONS BY ANALYZING INTRACARDIAC SIGNALS PROVIDING A DETAILED MAP AND DETERMINING POTENTIAL ABLATION POINTS

(71) Applicants: Biosense Webster (Israel) Ltd., Yokneam (IL); Carlo Pappone, Cernusco Lombardone (IT)

(72) Inventors: Carlo Pappone, Cernusco Lombardone (IT); Aharon Turgeman, Zichron Yaacov (IL); Paolo Roberto Pozzi, Limbiate (IT); Andrea Natalizia, Rome (IT)

(73) Assignee: Biosense Webster (Israel) Ltd., Yokneam (IL)

( * ) Notice: Subject to any disclaimer, the term of this patent is extended or adjusted under 35 U.S.C. 154(b) by 590 days.

(21) Appl. No.: 15/854,492

(22) Filed: Dec. 26, 2017

(65) Prior Publication Data

US 2018/0206920 A1    Jul. 26, 2018

Related U.S. Application Data

(60) Provisional application No. 62/450,381, filed on Jan. 25, 2017.

(51) Int. Cl.
*A61B 18/12* (2006.01)
*A61B 34/10* (2016.01)
(Continued)

(52) U.S. Cl.
CPC .............. *A61B 34/10* (2016.02); *A61B 5/283* (2021.01); *A61B 5/316* (2021.01); *A61B 5/339* (2021.01);
(Continued)

(58) Field of Classification Search
CPC ...... A61B 18/1492; A61B 2018/00363; A61B 2018/00577; A61B 18/00839;
(Continued)

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| EP | 2901953 A1 | 8/2015 |
| WO | 03/011112 A2 | 2/2003 |

(Continued)

OTHER PUBLICATIONS

European Search Report for Application No. 18153220.1 dated Jun. 7, 2018.

(Continued)

*Primary Examiner* — Daniel W Fowler

(57) ABSTRACT

A system and method for improving ablation procedures is presented. The method may comprise measuring EGM signals; performing three dimensional mapping of the EGM signals; and detecting a location for ablation based on the mapping. The method may further comprise creating a potential duration map, a local activation time map, and a bipolar voltage map. The method may further comprise creating a PDM by defining a window of interest (WOI) comprising at least a cycle length; calculating previous heart beats based on the cycle length and reference annotation; and assigning the heart beats within the cycle length of the WOI to the WOI. The method may further comprise detecting a location for ablation by finding start and end potential durations for the WOI; calculating a potential duration value (Continued)

using the start and end potential durations; selecting an ablation point; and using the selected ablation point as the detected location.

14 Claims, 14 Drawing Sheets

(51) Int. Cl.
| | |
|---|---|
| A61B 18/14 | (2006.01) |
| A61B 5/00 | (2006.01) |
| A61B 5/283 | (2021.01) |
| A61B 5/316 | (2021.01) |
| A61B 5/339 | (2021.01) |
| A61B 5/349 | (2021.01) |
| A61B 18/00 | (2006.01) |

(52) U.S. Cl.
CPC ............ *A61B 5/349* (2021.01); *A61B 5/6869* (2013.01); *A61B 5/743* (2013.01); *A61B 18/1492* (2013.01); A61B 2018/00363 (2013.01); A61B 2018/00577 (2013.01); A61B 2018/00839 (2013.01); A61B 2018/00904 (2013.01); A61B 2034/107 (2016.02)

(58) Field of Classification Search
CPC ...... A61B 2018/00904; A61B 2034/10; A61B 5/04012; A61B 5/042; A61B 5/044; A61B 5/0452; A61B 5/6869; A61B 5/743
See application file for complete search history.

(56) References Cited

U.S. PATENT DOCUMENTS

| | | | |
|---|---|---|---|
| 5,558,091 A | 9/1996 | Acker et al. | |
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,266,551 B1 | 7/2001 | Osadchy et al. | |
| 6,456,828 B1 | 9/2002 | Ozluturk | |
| 6,633,773 B1 * | 10/2003 | Reisfeld ............... | A61B 5/06 382/128 |
| 6,690,963 B2 | 2/2004 | Ben-Haim et al. | |
| 6,694,178 B1 | 2/2004 | Soula et al. | |
| 6,788,967 B2 | 9/2004 | Ben-Haim et al. | |
| 8,010,186 B1 * | 8/2011 | Ryu ..................... | A61B 5/6852 600/509 |
| 2004/0059237 A1 | 3/2004 | Narayan et al. | |
| 2005/0010201 A1 | 1/2005 | Abboud et al. | |
| 2005/0177049 A1 | 8/2005 | Hardahl et al. | |
| 2006/0058693 A1 | 3/2006 | Beatty et al. | |
| 2008/0009758 A1 * | 1/2008 | Voth ..................... | A61B 5/042 600/523 |
| 2009/0093806 A1 | 4/2009 | Govari et al. | |
| 2009/0099468 A1 | 4/2009 | Thiagalingam et al. | |
| 2009/0137916 A1 | 5/2009 | Maison-Blanche et al. | |
| 2009/0138007 A1 | 5/2009 | Govari et al. | |
| 2013/0116681 A1 | 5/2013 | Zhang | |
| 2013/0338518 A1 | 12/2013 | Zoica | |
| 2014/0081262 A1 | 3/2014 | Koblish et al. | |
| 2015/0238102 A1 | 8/2015 | Rubinstein et al. | |

FOREIGN PATENT DOCUMENTS

| | | |
|---|---|---|
| WO | 2006/066324 A1 | 6/2006 |
| WO | 2013123549 A1 | 2/2013 |
| WO | 2016/123390 A1 | 8/2016 |

OTHER PUBLICATIONS

Zhang et al., "Characterization of the epicardial substrate for catheter ablation of Brugada syndrome," Heart Rhythm, 2016, pp. 2151-2158, vol. 13, No. 11.

Munoz et al., Teaching Points With 3-Dimensional Mapping of Cardiac Arrhythmias, Circ Arrhythm Electrophysiol., 2011, 4:e22-e25.

Circ Arrhythm Electrophysiol. May 2017;10(5):e005053. doi: 10.1161/CIRCEP.117.005053.

* cited by examiner

METHOD AND SYSTEM FOR ELIMINATING A BROAD RANGE OF CARDIAC CONDITIONS BY ANALYZING INTRACARDIAC SIGNALS PROVIDING A DETAILED MAP AND DETERMINING POTENTIAL ABLATION POINTS

CROSS REFERENCE TO RELATED APPLICATION

This application incorporates by reference as if fully set forth Ser. No. 15/854,485 USNP titled "ANALYZING AND MAPPING ECG SIGNALS AND DETERMINING ABLATION POINTS TO ELIMINATE BRUGADA SYNDROME" filed on the same date as the present application. This application claims benefit of U.S. Provisional Application No. 62/450,381, filed on Jan. 25, 2017, which is incorporated by reference as if fully set forth.

SUMMARY

There is provided according to embodiments of the invention a system and method that enables improved analysis of electrogram (EGM) signals to determine potential ablation targets. The inventive system and method creates a detailed map, such as a potential duration map, by automatically measuring signals duration and annotating intracardiac EGM duration from onset to offset, and can determine potential ablation points in accordance with the detailed map.

A system and method for improving ablation procedures may comprise measuring EGM signals; performing three dimensional mapping of the EGM signals; and detecting a location for ablation based on the mapping.

In one embodiment, the method may further comprise creating one or more of a potential duration map (PDM), a local activation time (LAT) map, and a bipolar voltage map. In one embodiment, steps of defining a window of interest (WOI) comprising at least a cycle length; calculating previous heart beats based on the cycle length and reference annotation; and assigning the heart beats within the cycle length of the WOI to the WOI may be performed. In one embodiment, steps of finding a start potential duration for the WOI; finding an end potential duration for the WOI; calculating a potential duration value as a difference between the start potential duration and the end potential duration; selecting an ablation point based on a heart beat having a minimum standard deviation of the potential duration value; and using location of the selected ablation point as the detected location may be performed.

In one embodiment, finding a start potential duration may comprise setting a current peak from the list of peaks in the WOI; determining whether or not two consecutive peaks with same sign and same peaks absolute value are less than 2*Min; when the two consecutive peaks have the same sign and the same absolute value less than 2*Min, setting second peaks as the current peak, and obtaining next peak; and when the two consecutive peaks do not have the same sign or the same absolute value less than 2*Min, finding start of the slope before the current peak and marking the start of the slope as the start potential duration. In one embodiment, finding an end potential duration may comprise determining whether or not two consecutive peaks duration is greater than a predetermined duration; when the two consecutive peaks duration is greater than the predetermined duration, marking start of potential duration end current peak with minimum time of the two consecutive peaks; when the two consecutive peaks duration is less than or equal to the predetermined duration and when two consecutive peaks with the same sign and absolute value less than 2*Min or the time between two consecutive peaks is greater than the predetermined duration or the time between two consecutive peaks is less than a predetermined amount, obtaining a next peak with minimum time; and when the two consecutive peaks duration is less than or equal to the predetermined duration and when two consecutive peaks with the same sign and absolute value greater than or equal to 2*Min or the time between two consecutive peaks is less than or equal to the predetermined duration or the time between two consecutive peaks is greater than or equal to a predetermined amount, finding the start of the slope after the current peak and marking the start of the slope after the current peak as end potential duration.

In one embodiment, three dimensional mapping may comprise creating a color mapping.

A computer program product for improving an ablation process is also presented.

These and other objects, features and advantages of the present invention will be apparent from the following detailed description of illustrative embodiments thereof, which is to be read in connection with the accompanying drawings.

BRIEF DESCRIPTION OF THE DRAWINGS

The present invention is illustrated by way of example, and not by way of limitation, in the figures of the accompanying drawings in which.

DETAILED DESCRIPTION

Figure 1A:
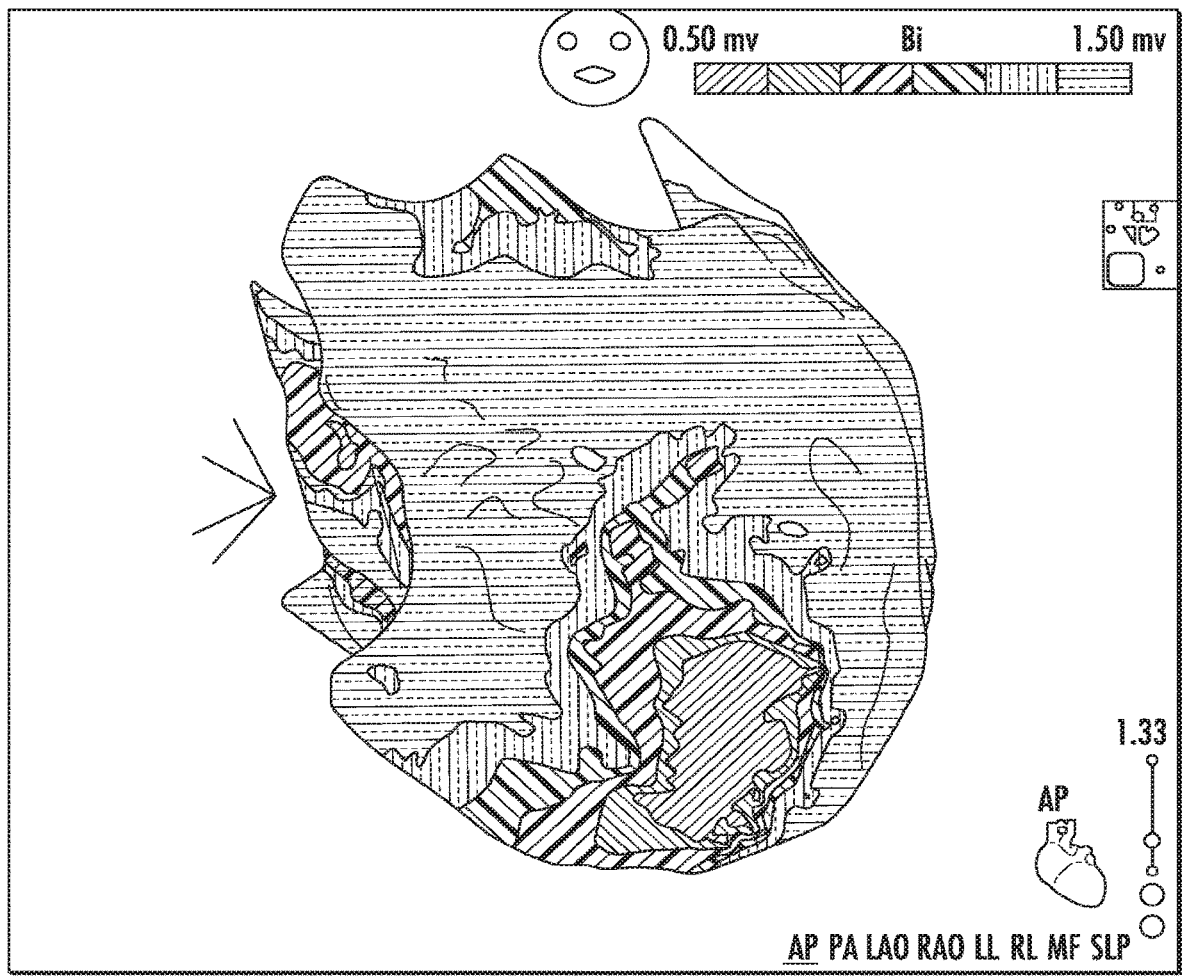
FIGS. 1A and 1B show Clinical Use—Post-Ischemic Ventricular Tachycardia in one embodiment.

Cardiac electrophysiological procedures have become increasingly complex as clinicians treat challenging conditions such as atrial fibrillation and ventricular tachycardia. The treatment of complex arrhythmias currently relies on the use of three dimensional (3D) mapping systems in order to reconstruct the anatomy of the heart chamber of interest. Cardiac mapping, for example, creating a map of electrical potentials (a voltage map) of the wave propagation along the heart tissue or a map of arrival times (a local time activation (LAT) map) to various tissue located points may be used for detecting local heart tissue dysfunction For example, cardiologists rely upon software such as the Complex Fractionated Atrial Electrograms (CFAE) module of the CARTO®3 3D mapping system, produced by Biosense Webster, Inc. (Diamond Bar, Calif.), to analyze intracardiac EGM signals and determine the ablation points for treatment of a broad range of cardiac conditions, including atypical atrial flutter and ventricular tachycardia. The software maps the cardiac abnormality potential in the heart with a time-consuming process of manual measurements (performed by the physician) to create a duration map, used to identify ablation targets. For example, in this time-consuming process, the physician must move the two duration calipers for each point taken during map construction.

The 3D maps provide multiple pieces of information regarding the electrophysiological properties of the tissue that represent the anatomical and functional substrate of these challenging arrhythmias. However, the 3D reconstruction requires collection of a huge amount of electrical data from different regions and this process is slow, time-consuming and labor intensive, often requiring obtaining more than 150-200 points.

Cardiomyopathies with different etiologies (ischemic, dilated cardiomyopathy (DCM), hypertrophic cardiomyopathy (HCM), arrhythmogenic right ventricular dysplasia (ARVD), left ventricular non-compaction (LVNC), etc.) have an identifiable substrate, featured by areas of unhealthy tissue surrounded by areas of normally functioning cardiomyocytes. Abnormal tissue is generally characterized by low-voltage EGMs. However, initial clinical experience in endo-epicardial mapping indicates that areas of low-voltage are not always present as the sole arrhythmogenic mechanism in such patients. In fact, areas of low or medium-voltage may exhibit EGM fragmentation and prolonged activities during sinus rhythm, which corresponds to the critical isthmus identified during sustained and organized ventricular arrhythmias, e.g., applies only to non-tolerated ventricular tachycardias. Moreover, in many cases, EGM fragmentation and prolonged activities are observed in the regions showing a normal or near-normal voltage amplitude (>1-1.5 mV). Although the latter areas may be evaluated according to the voltage amplitude, they cannot be considered as normal according to the intracardiac signal, thus representing a true arrhythmogenic substrate. The 3D mapping is able to localize the arrhythmogenic substrate on the endocardial and/or epicardial layer of the right/left ventricle, which may vary in distribution according to the extension of the main disease.

The substrate linked to these cardiac conditions is related to the presence of fragmented and prolonged EGMs in the endocardial and/or epicardial layers of the ventricular chambers (right and left). The 3D mapping system, such as CARTO®3, is able to localize the potential arrhythmogenic substrate of the cardiomyopathy in terms of abnormal EGM detection.

Accordingly, the appropriate characterization of the abnormal substrate along with the localization of such EGMs is crucial to establish the appropriate target for catheter ablation in order to achieve a successful procedure.

FIGS. 1-6 show a mapping technique, the PDM, which is performed to visualize the abnormal substrate according to the EGMs duration found on the endocardial/epicardial tissue. Such an approach needs an appropriate definition of the electrophysiological substrate, characterized by prolonged and fragmented EGMs. In this setting, elimination of these EGMs by catheter ablation may result in ventricular arrhythmia suppression during the procedure and prevention of sudden death in the follow up.

The inventive annotation method and system presented herein is an improvement upon the existing time-consuming process of manual measurements for duration map construction. The physician no longer needs to manually move and measure the two duration calipers for each point taken during duration map construction. Instead, the present method automatically annotates the ventricular EGMs duration from the onset to its offset, and automatically measures signals duration to create the potential duration map in order to potentially identify the arrhythmogenic substrate related to each cardiomyopathy. This enables automation of the process of detecting a potential target for ablation. The inventors' data indicates that epicardial ablation can be useful in symptomatic high-risk patients, offering a preventing therapy for certain heart condition. Epicardial ablation can be useful in symptomatic high-risk patients, offering a preventive therapy for certain heart conditions. Thus, the present system and method enables improved detection and treatment of atypical atrial flutter and ventricular tachycardia (VT).

Figure 1B:
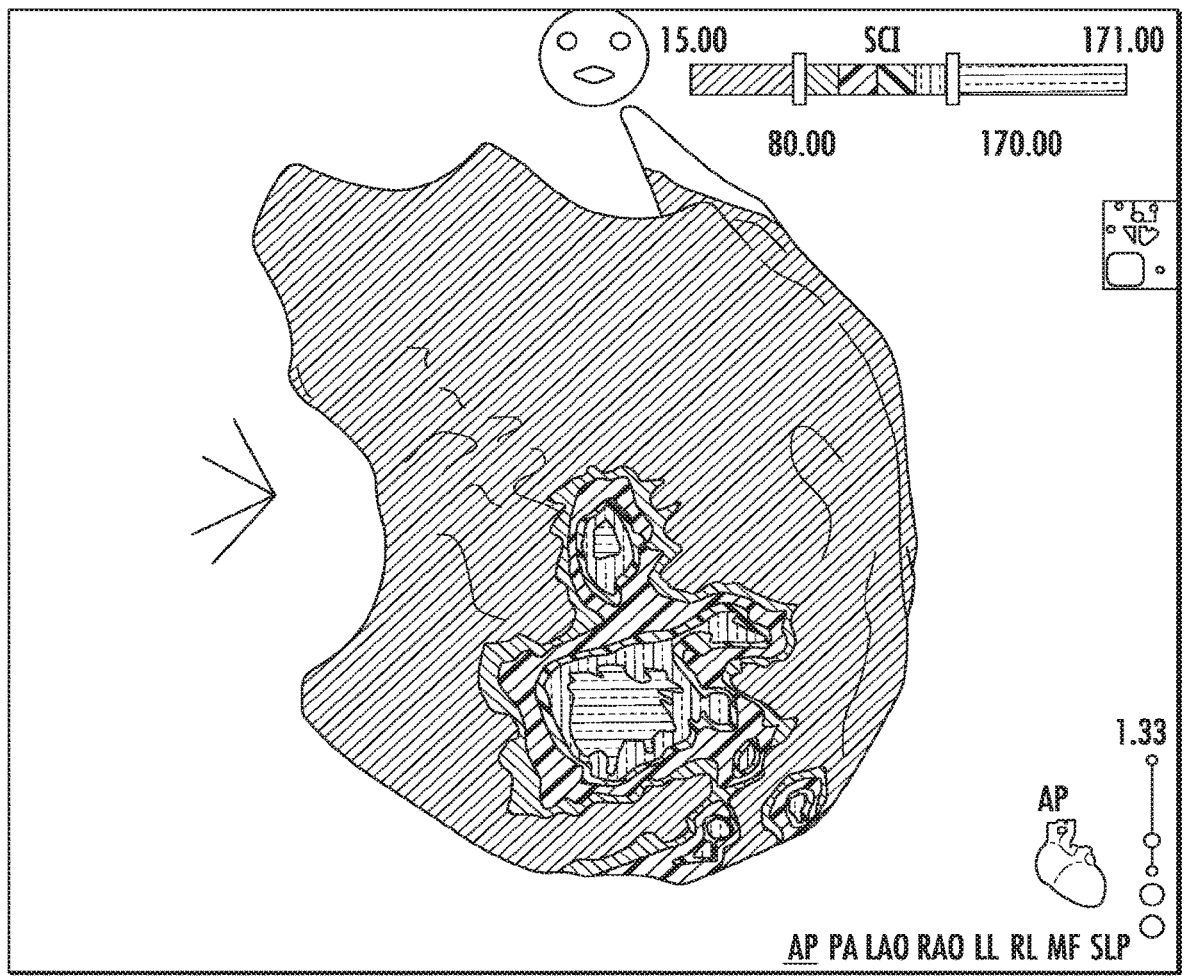
Figure 2:
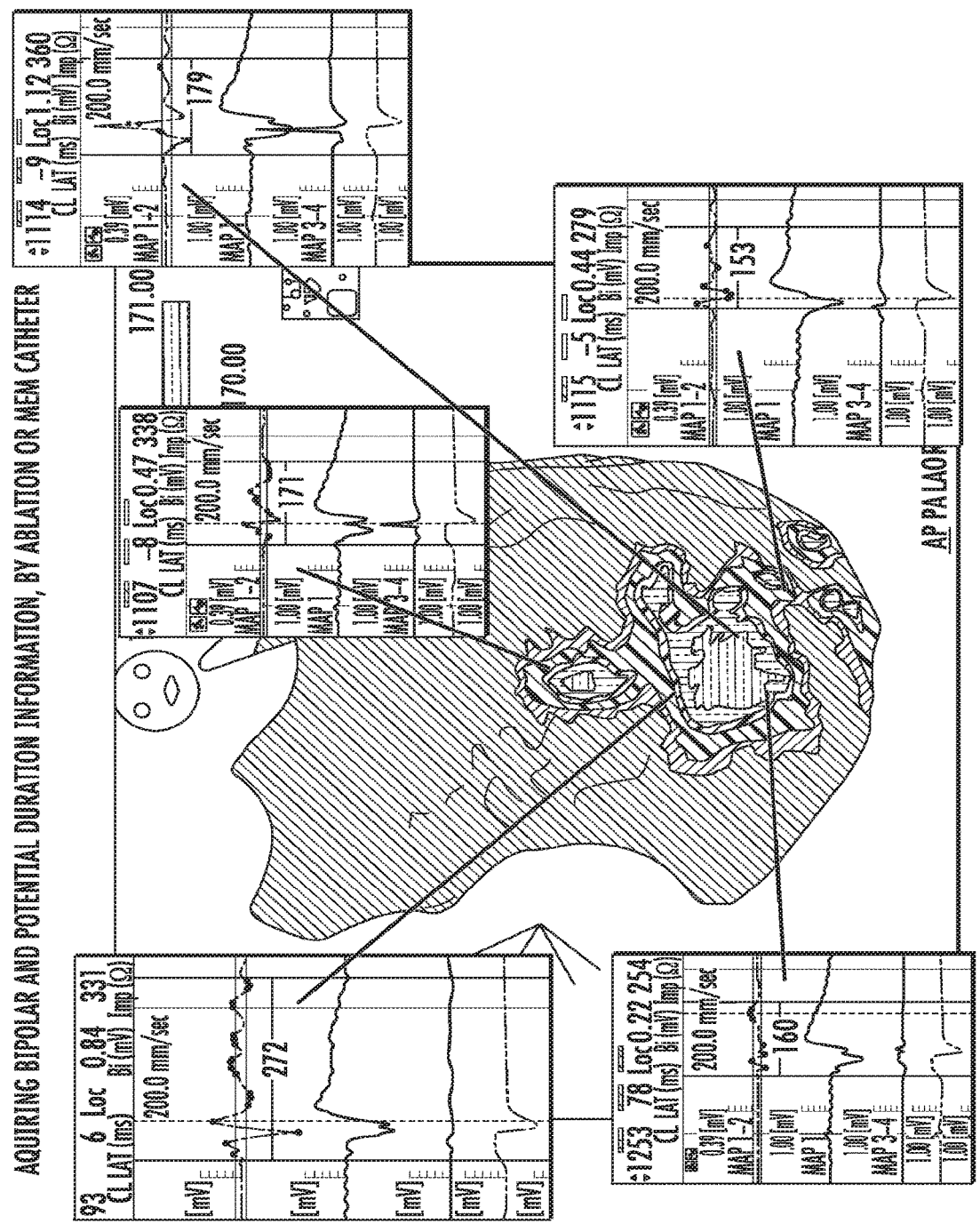
FIG. 2 shows Clinical Use—Post-Ischemic Ventricular Tachycardia in another embodiment.

As seen in the PDMs shown in FIGS. 1A, 1B and 2, the present technique can be applied to measure any prolonged potential inside or around the dense scar area, which can help to identify any possible functional channel sustaining VT. FIGS. 1A, 1B and 2 each show post-ischemic VT characterized by endo-epicardial low or intermediate voltage area in which signal conduction is slowed down. This illustrates that measuring any prolonged potential inside or around the dense scar area may help identify potential isthmuses sustaining VT.

FIGS. 1A, 1B and 2 also illustrate substrate mapping acquiring bipolar and potential duration information by ablation or multi-electrode (MEM) catheter. FIG. 1A illustrates the bipolar signal amplitude (Bi) variance in the various sectors of the heart; FIG. 1A shows Bi ranges from 0.5 mV to 1.5 mV. FIG. 1B illustrates the Shortex Complex Interval (SCI) variance in the various sectors of the heart; SCI ranges from 15.0 msec to 171.00 msec with the SCI range of interest between 80 msec and 170 msec. FIG. 2 shows the EGM graphs associated with five distinct portions of the heart; these five portions are located within the critical area having Bi between 0.5 mV and 1.0 mV and SCI between 80 msec and 170 msec. The EGMs shown in FIG. 2 can be identified by MAP 1-2 or MAP 3-4.

Figure 3A:
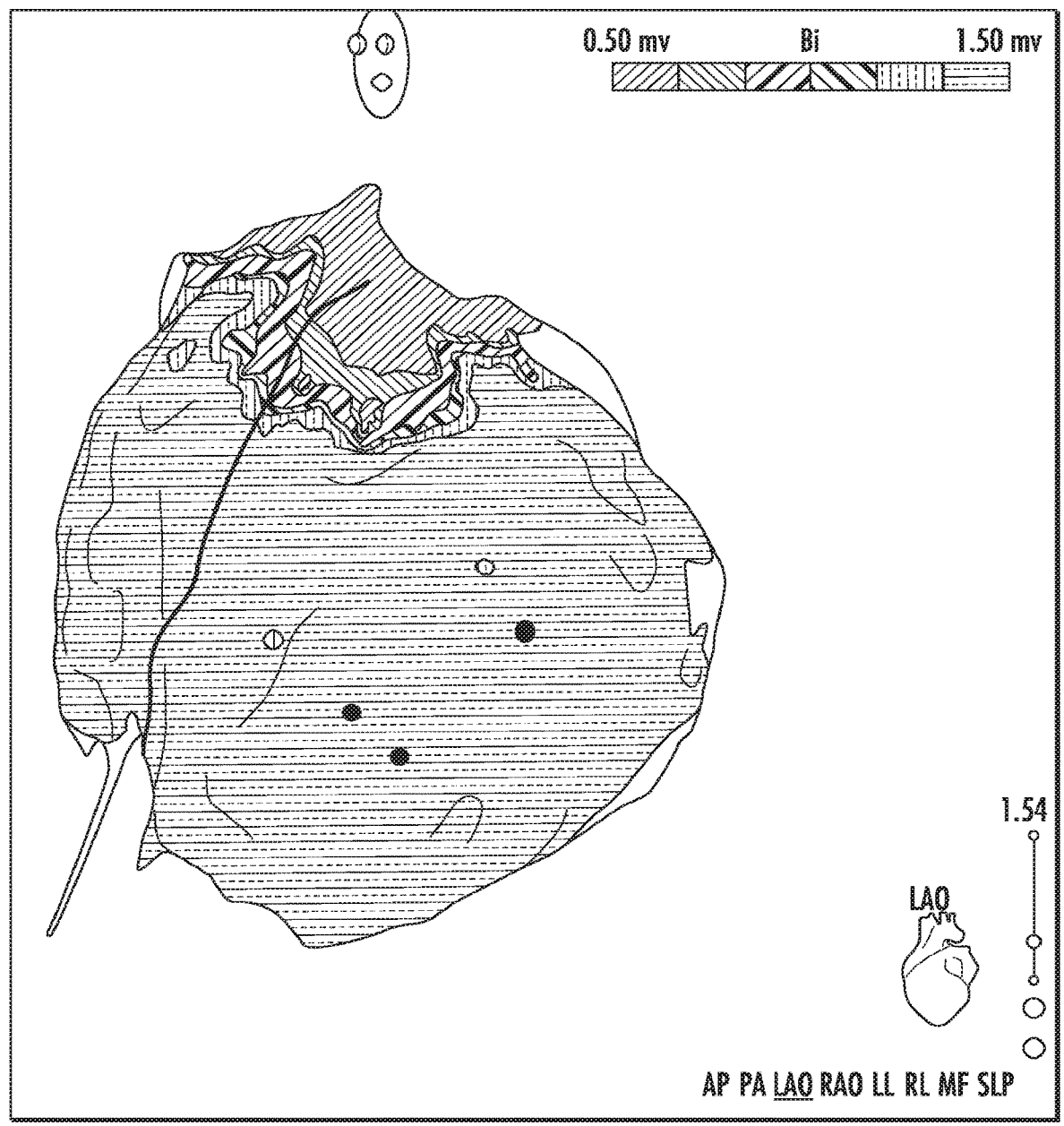
FIGS. 3A and 3B show Clinical Use—Left Ventricular Non Compaction Cardiomyopathy in one embodiment.
Figure 3B:
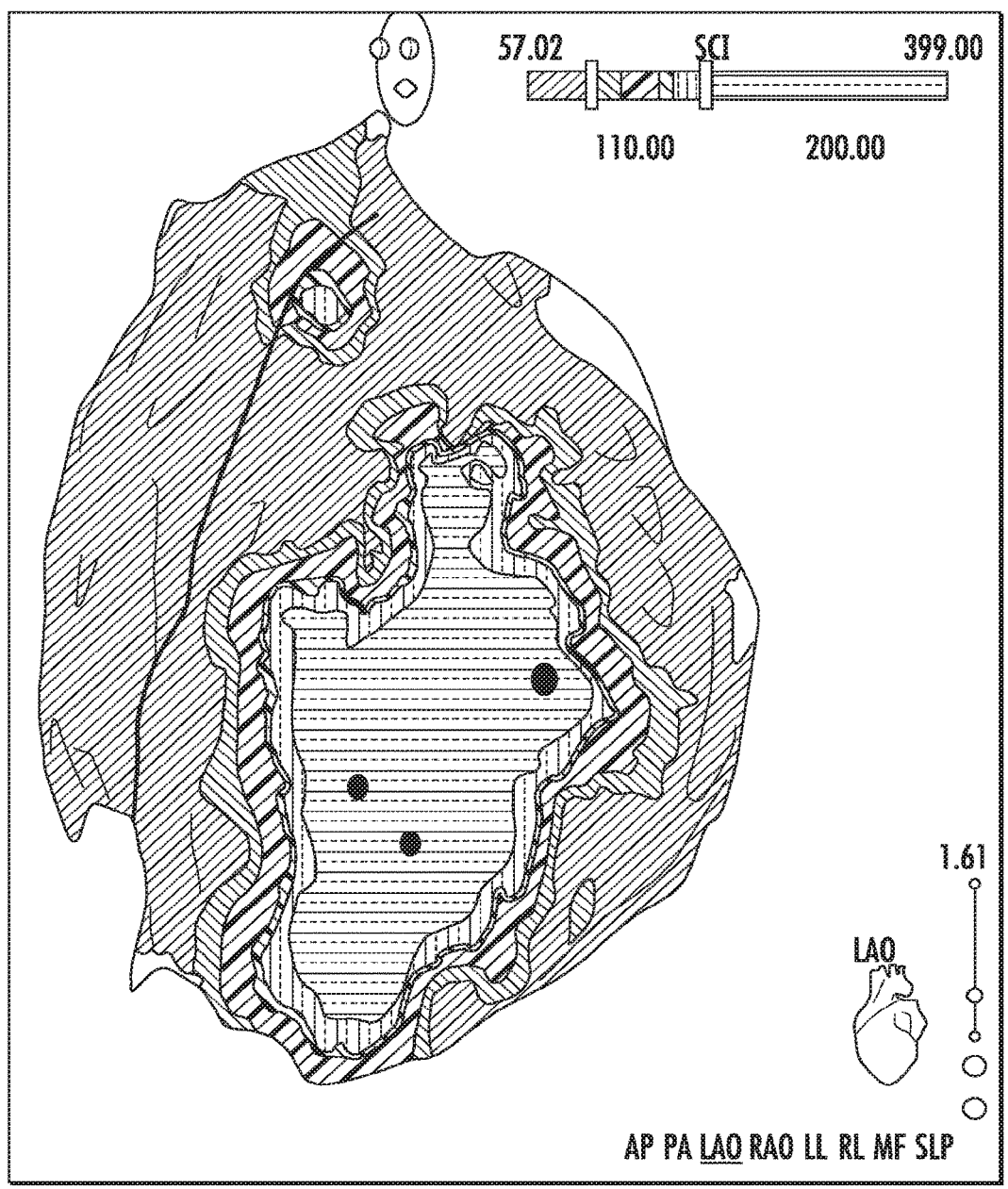
Figure 4:
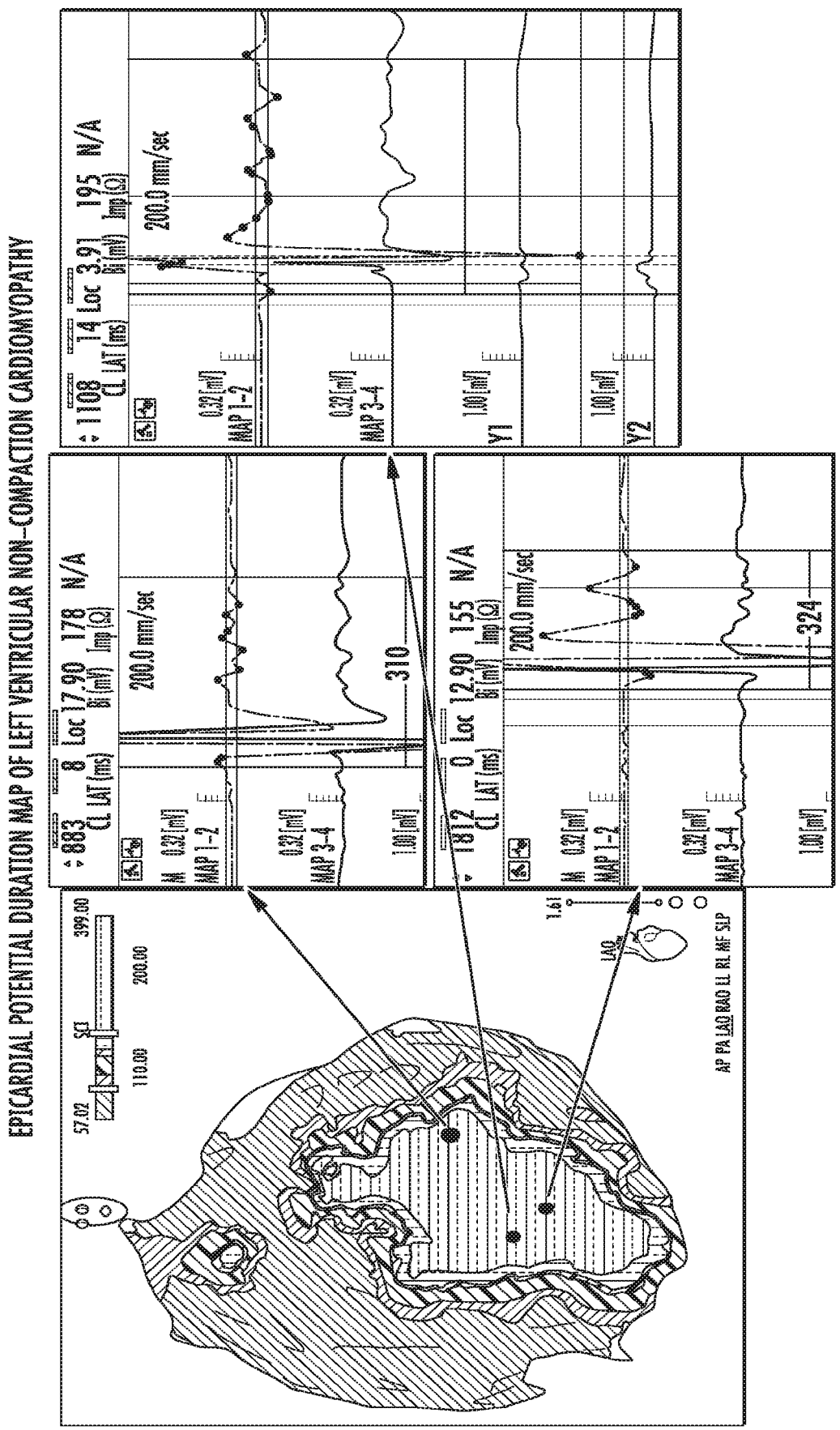
FIG. 4 shows Clinical Use—Left Ventricular Non Compaction Cardiomyopathy in one embodiment (with EGM).

Illustrating left ventricle non-compaction cardiomyopathy, FIG. 3A shows an epicardial voltage map and FIG. 3B shows PDM. The three black circles in FIGS. 3A and 3B are marked as abnormally prolonged potentials, e.g., potentials above 200 msec. FIG. 4 shows epicardial PDM of left ventricle non-compaction cardiomyopathy. Of note, typical ventricular fragmented and prolonged potentials are shown with an initial component characterized by normal (>1.5 mV) amplitude. The EGMs of interest, e.g., those having abnormally prolonged potentials (shown as black circles), can be identified by MAP 1-2 or MAP 3-4 in FIG. 4.

Figure 5A:
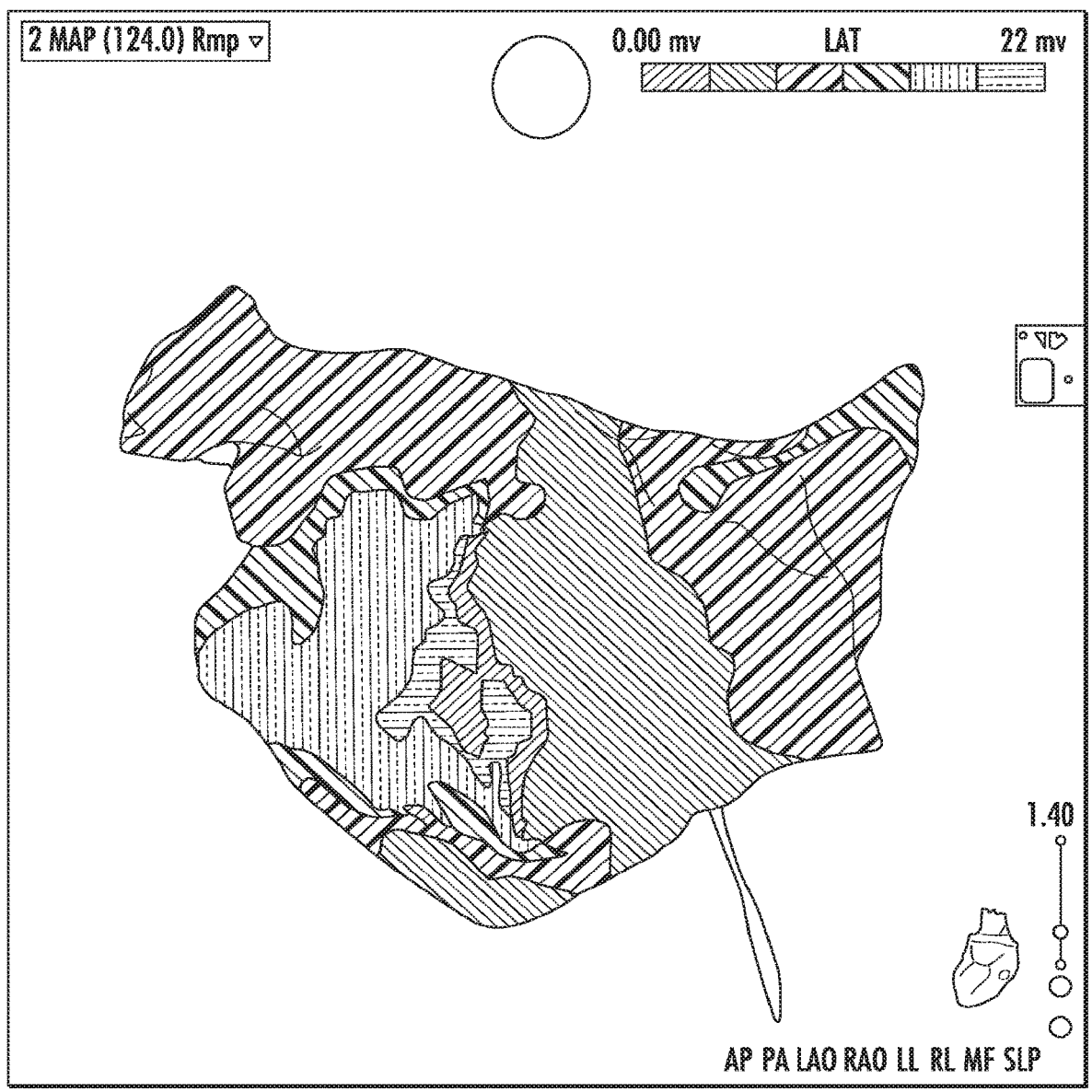
FIGS. 5A and 5B show Clinical Use—Atypical Atrial Flutter.
Figure 5B:
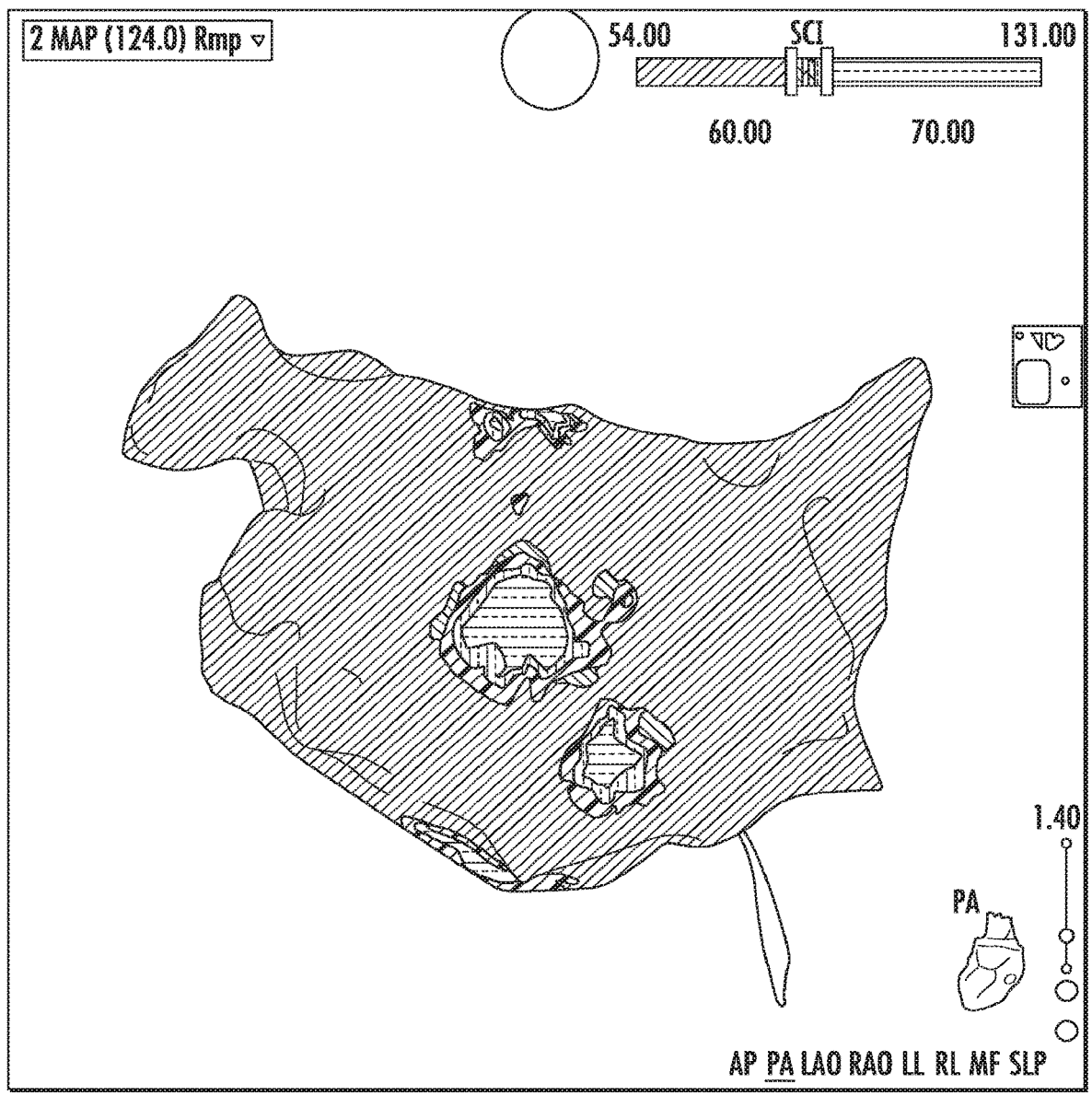
Figure 6:
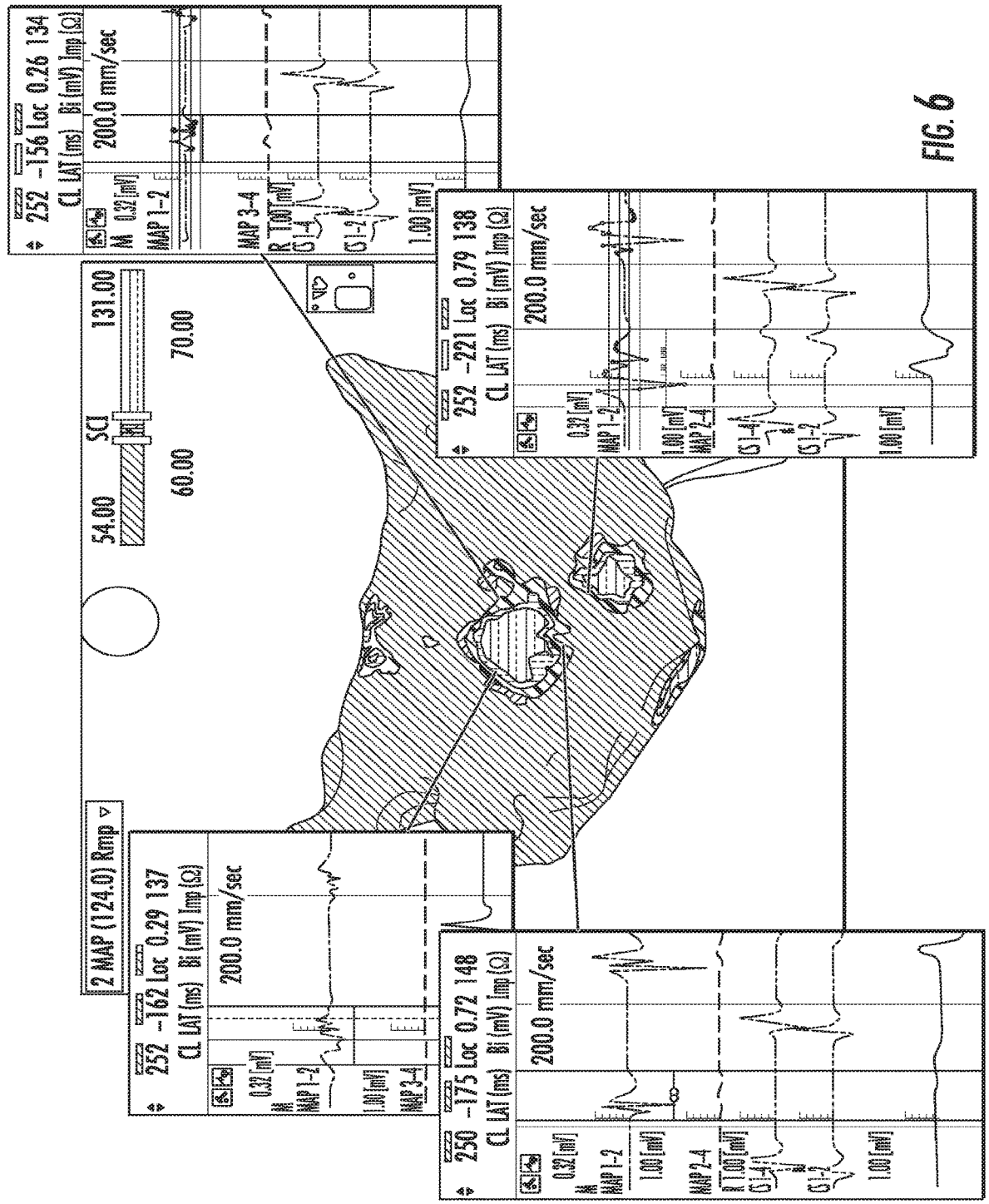
FIG. 6 shows Clinical Use—Atypical Atrial Flutter ("color bar" threshold set according to the case).

The application of the system to atypical atrial flutter and mapping during tachycardia is illustrated in FIGS. 5A, 5B and 6. Once the critical isthmus has been identified, one may focus on any fragmented signal along it, as any such signal may represent a critical isthmus for the sustained tachycardia. In these figures, mapping is performed during tachycardia. Moreover, one can differentiate between local activation time (LAT) windows of interest (WOI) and PDM WOI. A specific WOI for LAT and a different WOI for PDM can be set. During tachycardia, a mesodiastolic WOI is set for mapping the atrial re-entrant tachycardia. Note that some part of a fragmented potential can fall partially outside the LAT WOI. In such cases, only the signal portion inside the LAT WOI would be annotated in the PDM. Of note, FIG. 6 shows typical fragmented and prolonged mesodiastolic potentials identified during atrial tachycardia; note that one may set the color bar threshold according to the case. The EGMs shown in FIG. 6 can be identified by MAP 1-2 or MAP 3-4.

Figure 7:
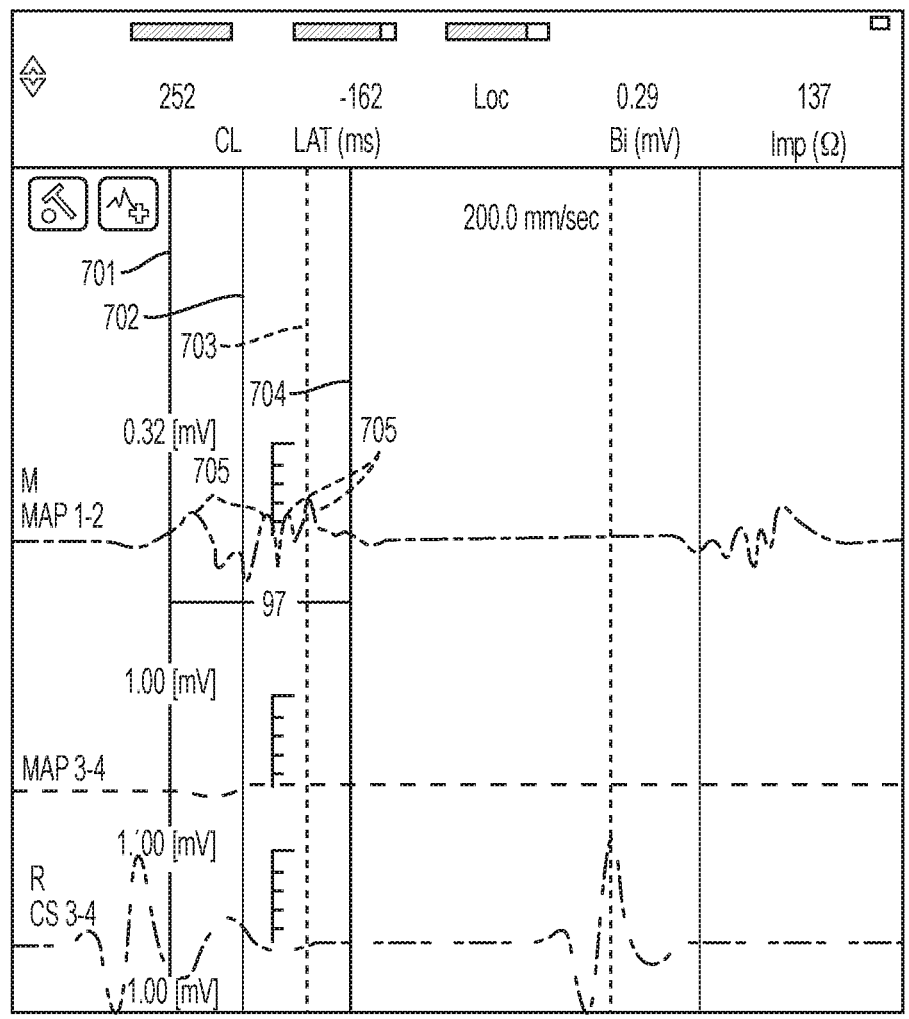
FIG. 7 shows a Potential Duration Map in one embodiment.

FIG. 7 is an EGM which shows a mesodiastolic potential. As the LAT WOI cannot be modified depending on fragmentation of potentials during tachycardia, setting two different WOI can be useful. FIG. 7 shows vertical lines 701, 702, 703, 704 that border example WOIs. Accordingly, one WOI can exist between lines 701 and 702 and a second WOI can exist between lines 703 and 704. In addition, peaks 705 of the EGM are annotated. Currently the potential can be measured using the CARTO®3 CFAE module by manually annotating the duration outside the LAT WOI. In the present system, automated annotation can be performed.

Figure 8:
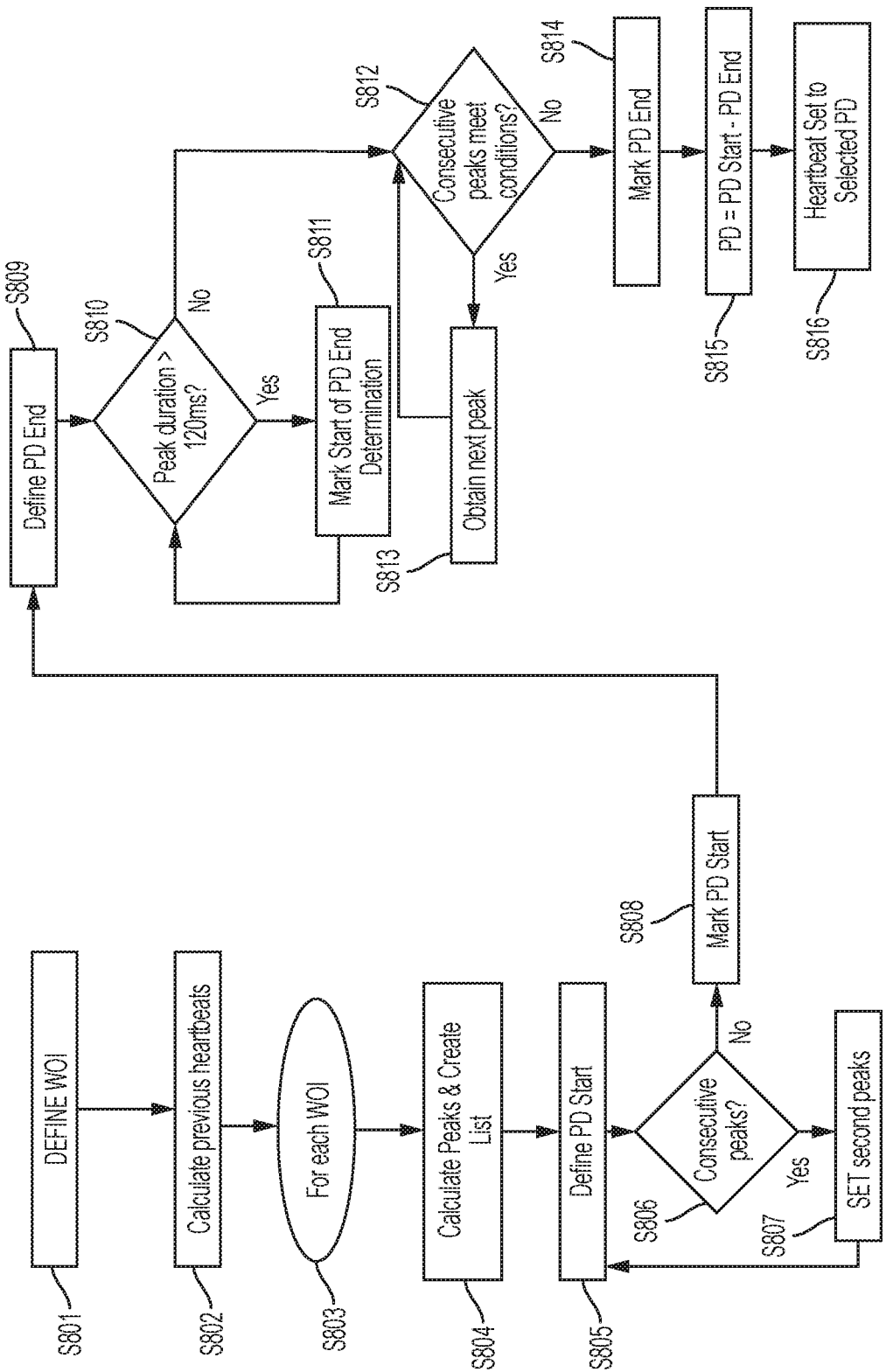
FIG. 8 shows a flow diagram of an exemplary method in an embodiment of the invention.

FIG. 8 is a flow diagram of an example method in an embodiment of the invention. The EGM of FIG. 7 may be used to illustrate the embodiment shown in FIG. 8. As shown in FIG. 8, the example method is performed as follows:

In step S801, define Window Of Interest (WOI) which is the interval in the EGM and/or ECG which is normally used to calculate the voltage amplitude, [peak to peak mV] and the signal duration. The WOI can be set according to the arrhythmia. For example, the WOI for atrial flutter can be from −70 ms to 230 ms if the cycle length is 250 ms. In atypical atrial flutter, differentiation is made between LAT WOI and PDM WOI, as discussed above.

In step S802, calculate at least two previous heart beats based on cycle length and reference annotation, and assign WOI for both heart beats. Note that each electroanatomical acquired point (e.g., point EGM) contains data to be used for coloring the Map according to Map Type, such as PDM, LAT, Bipolar Voltage etc. In one acquired point, for example, a window equal to 2500 ms of ECG and EGM is recorded. For example, if the reference annotation for a heartbeat lays at 2000 ms, the first WOI [−50 ms, 350 ms] goes from 2000 ms−50 ms (e.g., 1950 ms) to 2000 ms+350 ms (e.g., 2350 ms). If the heart beat cycle length is 800 ms, there is more than one heart beat in the 2500 ms. The previous heart beat reference lays at 1200 ms (2000 ms−800 ms [e.g., 1200 ms]) and the WOI will be from 1200 ms−50 ms (e.g., 1150 ms) to 1200 ms+350 ms (e.g., 1550 ms). It should be noted that the abovementioned time intervals have been used by way of example and should not be considered as limiting.

In step S803, for each WOI of each heartbeat, the Potential Duration is calculated as shown in steps S804-S814, as follows.

In step S804, calculate the heartbeat peaks based on a predetermined threshold in WOI and create a list of peaks in WOI. In one embodiment, the threshold for defining the peaks is +/−0.05 mV. The EGM signal values are measured in mV, and, in one example, a peak with mV value greater than 0.05 mV is marked. However, it should be noted that the peak threshold may be set by the physician. Typically the threshold is in accordance with the arrhythmia.

In step S805, Potential Duration Start is defined by checking from the beginning of WOI, as shown in steps S806-S808 as follows.

In step S806, determine whether two consecutive peaks have the same sign and the absolute value of both are less than 2*Min.

In step S807, if S806=YES (two consecutive peaks have the same sign and the absolute value of the consecutive peaks is less than 2*Min), set current peak as the second peak, obtain the next peak, and go to step S806.

In step S808, if S806=NO (two consecutive peaks do not have the same sign and/or the absolute value of either consecutive peak is greater than or equal to 2*Min), find start of the slope before the current peak and mark it as Start Potential Duration.

In step S809, Potential Duration End is defined, checking from the ending of WOI, as shown in steps S810-S814 as follows.

In step S810, determine whether two consecutive peaks distance is greater than 120 ms.

In step S811, if S810=YES (two consecutive peaks have a distance greater than 120 ms), mark the start of Potential Duration End portion as the peak with minimum time of the two consecutive peaks and to go S810.

If S810=NO (two consecutive peaks do not have distance greater than 120 ms), then in step S812, determine whether two consecutive peaks have the same sign and both peaks absolute values are less than 2*Min Threshold or whether the time between two consecutive peaks is less than 25 ms. In addition, another filter may be taken into account for the automatic software. Stability and reproducibility of the duration of the potential can be crucial. In one embodiment, the system can verify, in presence of a double or late potential, that the late activity is also present in all the beats included in the 2500 ms recording window.

In step S813, if S812=YES (two consecutive peaks have the same sign and the peaks absolute values are less than 2*Min or the time between two consecutive peaks is greater than 120 ms or the time between two consecutive peaks is less than 25 ms), obtain next peak with minimum time, and go to S812.

In step S814, if S812=NO (two consecutive peaks do not have the same sign or the peaks absolute values are equal to or greater than 2*Min or the time between two consecutive peaks is less than or equal to than 120 ms or the time between two consecutive peaks is greater than or equal to 25 ms), find the start of the slope after the current peak and mark it as End Potential Duration.

In step S815, calculate Potential Duration Value as the difference between Potential Duration Start and Potential Duration End in ms.

In step S816, set the selected point potential duration value as the heart beat which has the minimum standard deviation of the positions on each heart beat WOI.

In accordance with the PDM and the above-described analysis, any EGM showing a duration ≥200 ms is considered abnormal, and thus represents the target for catheter ablation. Three different concentric areas are identified according to the degree of prolongation by setting different cut-off intervals. In Atypical Atrial Flutter, a duration of ≥70 ms can be marked as target for ablation. In Ischemic VT, a duration of ≥170 ms can targeted for ablation. In cardiomyopathies, a duration of ≥200 ms can be marked for ablation. The different cut-offs depend upon each patient condition and the type of arrhythmia treated. They can be used to guide the ablation procedure, but they are not to be considered as limiting.

Figure 9:
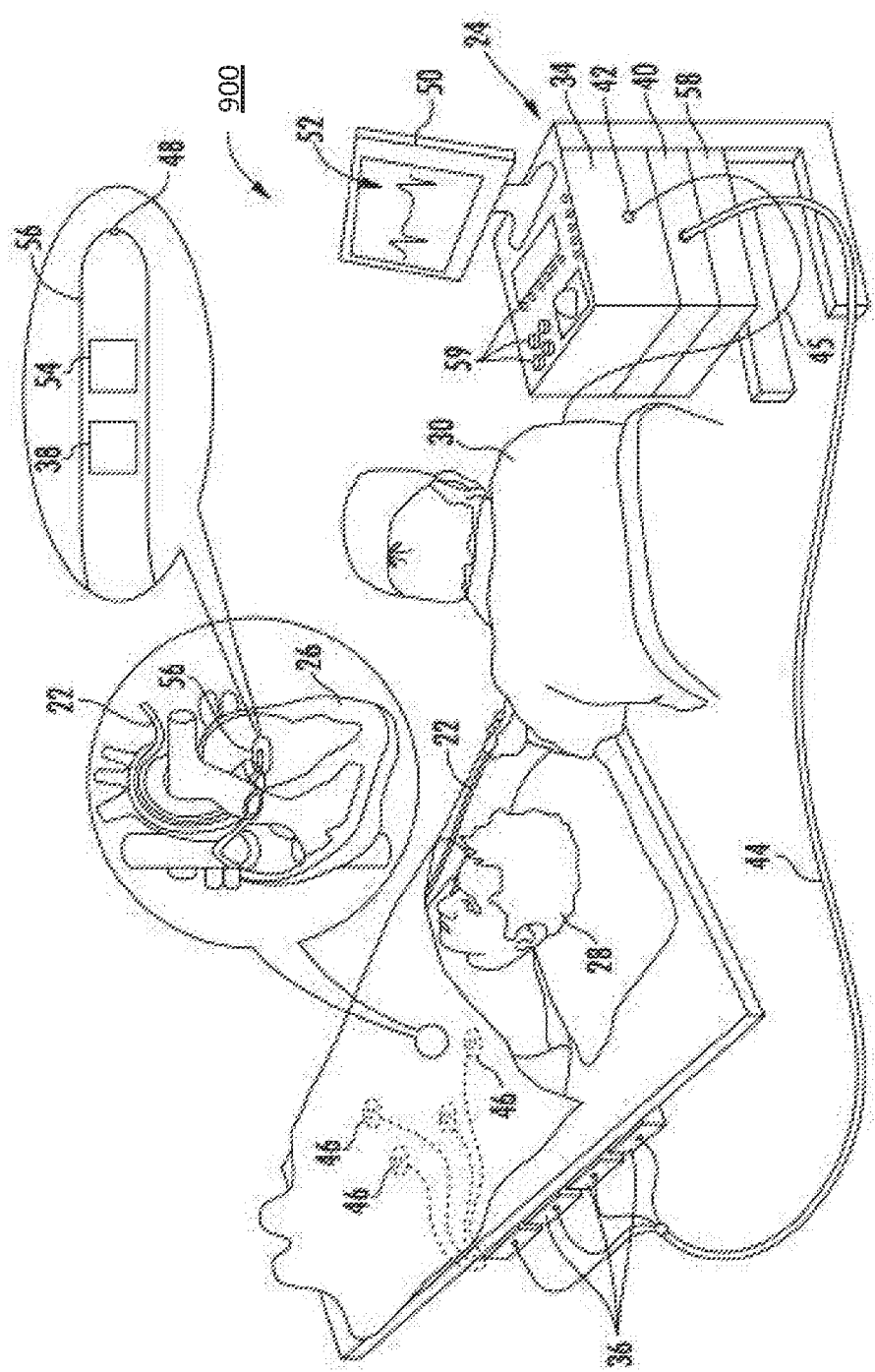
FIG. 9 shows an exemplary mapping system for real-time mapping of cardiac ablation in accordance with an embodiment of the present invention, in which the inventive technique is used.

FIG. 9 is an illustration of an example medical system 900 that may be used to generate and display information 52 (e.g., PDM and other maps and anatomical models of a portion of a patient and signal information). Tools, such as tool 22, can be any tool used for diagnostic or therapeutic treatment, such as for example, a catheter having a plurality of electrodes for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine 3-D position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 9), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 900 shown in FIG. 9, one or more emitter coils can be placed below the torso of the patient 28 and each configured to generate magnetic fields in a predefined working volume that contains the heart 26 of the patient.

As shown in FIG. 9, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 9 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO™ mapping system produced by Biosense Webster Inc., of Diamond Bar, Calif., and is described in detail in the patents and the patent applications cited herein.

The tool 22 may also include a force sensor 54 contained within the tip 56. The force sensor 54 may measure a force applied by the tool 22 (e.g., the tip 56 of the tool) to the endocardial tissue of the heart 26 and generate a signal that is sent to the control console 24. The force sensor 54 may include a magnetic field transmitter and a receiver connected by a spring in the tip 56, and may generate an indication of the force based on measuring a deflection of the spring. Further details of this sort of probe and force sensor are described in U.S. Patent Application Publications 2009/0093806 and 2009/0138007, whose disclosures are incorporated herein by reference. Alternatively, the tip 56 may include another type of force sensor that may use, for example, fiber optics or impedance measurements.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

Although the example medical system 900 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on the electrical impulses received from the body surface electrodes 46 and the electrical signals received from the tool 22 via the I/O interface 42 and other components of medical system 900, the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 9, the control console 24 is connected, via cable 44, to body surface electrodes 46, each of which are attached to patient 28 using patches (e.g., indicated in FIG. 9 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 900 may include a second operator that manipulates the control console 24 while the operator 30 manipulates the tool 22. It should be noted that the configuration shown in FIG. 9 is exemplary. Any suitable configuration of the medical system 900 may be used and implemented.

Figure 10:
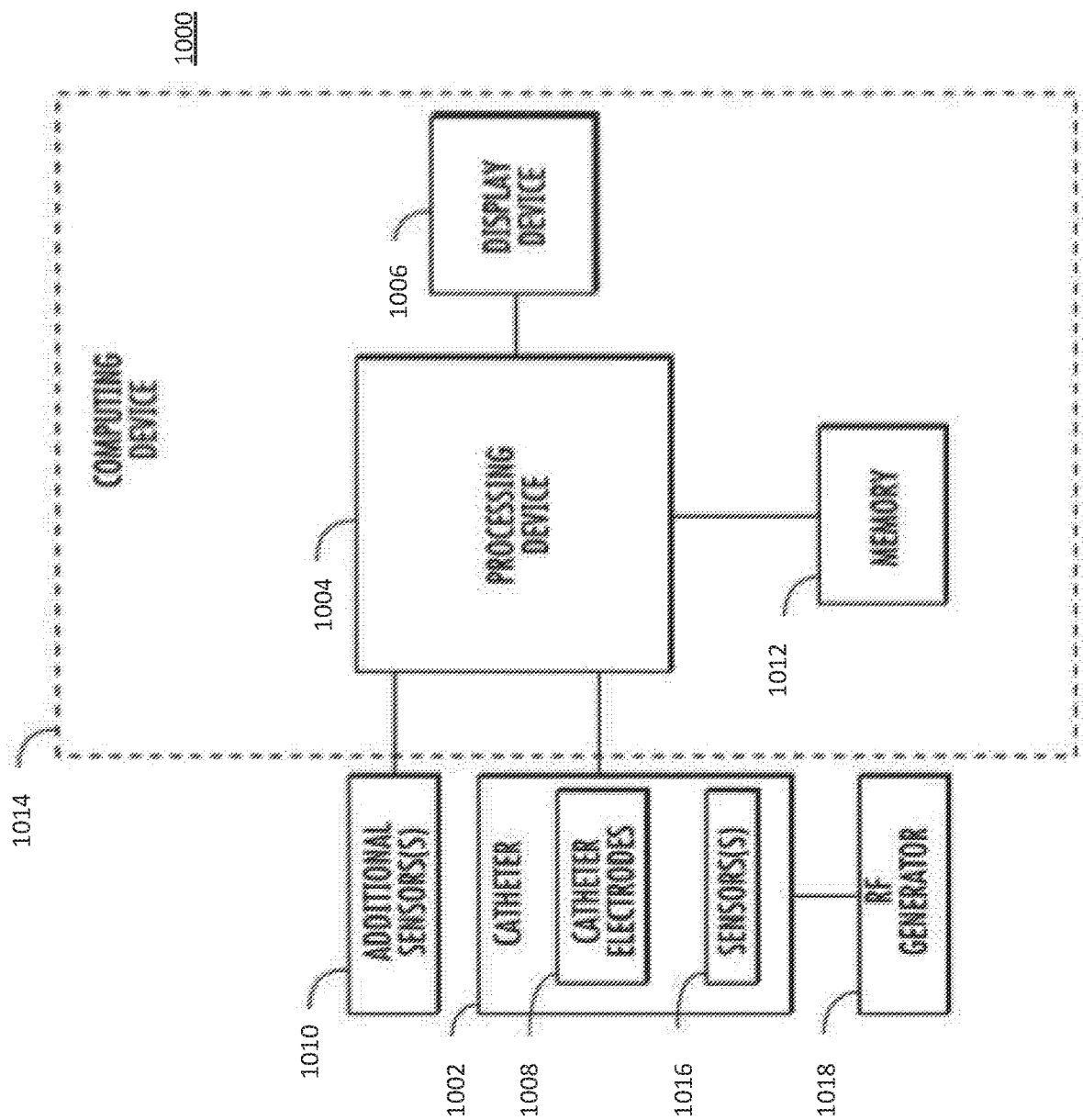
FIG. 10 is a block diagram illustrating example components of a medical system in one embodiment.

FIG. 10 is a block diagram illustrating example components of a medical system 1000 in which features described herein can be implemented. As shown in FIG. 10, the system 1000 includes catheter 1002, processing device 1004, display device 1006 and memory 1012. As shown in FIG. 10, the processing device 1004, display device 1006 and memory 1012 are a part of computing device 1014. In some embodiments, the display device 1006 may be separate from computing device 1014. Computing device 1014 may also include an I/O interface, such as I/O interface 42 shown in FIG. 9.

Catheter 1002 includes a plurality of catheter electrodes 1008 for detecting the electrical activity of the heart over time. Catheter 1002 also includes sensor(s) 1016, which include, for example, sensors (e.g., a magnetic field location sensor) for providing location signals to indicate the location of the catheter 1002 in a 3-D space as well as sensors (e.g., position sensors, pressure or force sensors, temperature sensors, impedance sensors) for providing ablation parameter signals during the ablation of the heart tissue. The example system 1000 also includes one or more additional sensors 1010, separate from the catheter 1002, used to provide location signals indicating the location of the catheter 1002 in a 3D space.

The system 1002 shown in example system 1000 also includes an RF generator 1018, which supplies high-frequency electrical energy, via catheter 1002, for ablating tissue at locations engaged by the catheter 1002. Accordingly, catheter 1002 may be used to acquire electrical activity for generating mapping of the heart as well ablating cardiac tissue. As described above, however, embodiments may include catheters used to acquire the electrical activity for generating mapping of the heart while not used to ablate cardiac tissue.

Processing device 1004 may include one or more processors each configured to process the ECG signals, record ECG signals over time, filter ECG signals, fractionate ECG signals into signal components (e.g., slopes, waves, complexes) and generate and combine ECG signal information for displaying the plurality of electrical signals on display device 1006. Processing device 1004 may also generate and interpolate mapping information for displaying maps of the heart on display device 1006. Processing device 1004 may include one or more processors (e.g., signal processor 40) configured to process the location information acquired from sensors (e.g., additional sensor(s) 1010 and catheter sensor(s) 1016) to determine location and orientation coordinates.

Processing device 1004 is also configured to drive display device 1006 to display dynamic maps (i.e., spatio-temporal maps) of the heart and the electrical activity of the heart using the mapping information and the ECG data. Display device 1006 may include one or more displays each configured to display maps of the heart representing spatio-temporal manifestations of the electrical activity of the heart over time and display the ECG signals acquired from the heart over time.

The catheter electrodes 1008, catheter sensor(s) 1016 and additional sensor(s) 1010 may be in wired or wireless communication with processing device 1004. Display device 1006 may also be in wired or wireless communication with processing device 1004.

Figure 11:
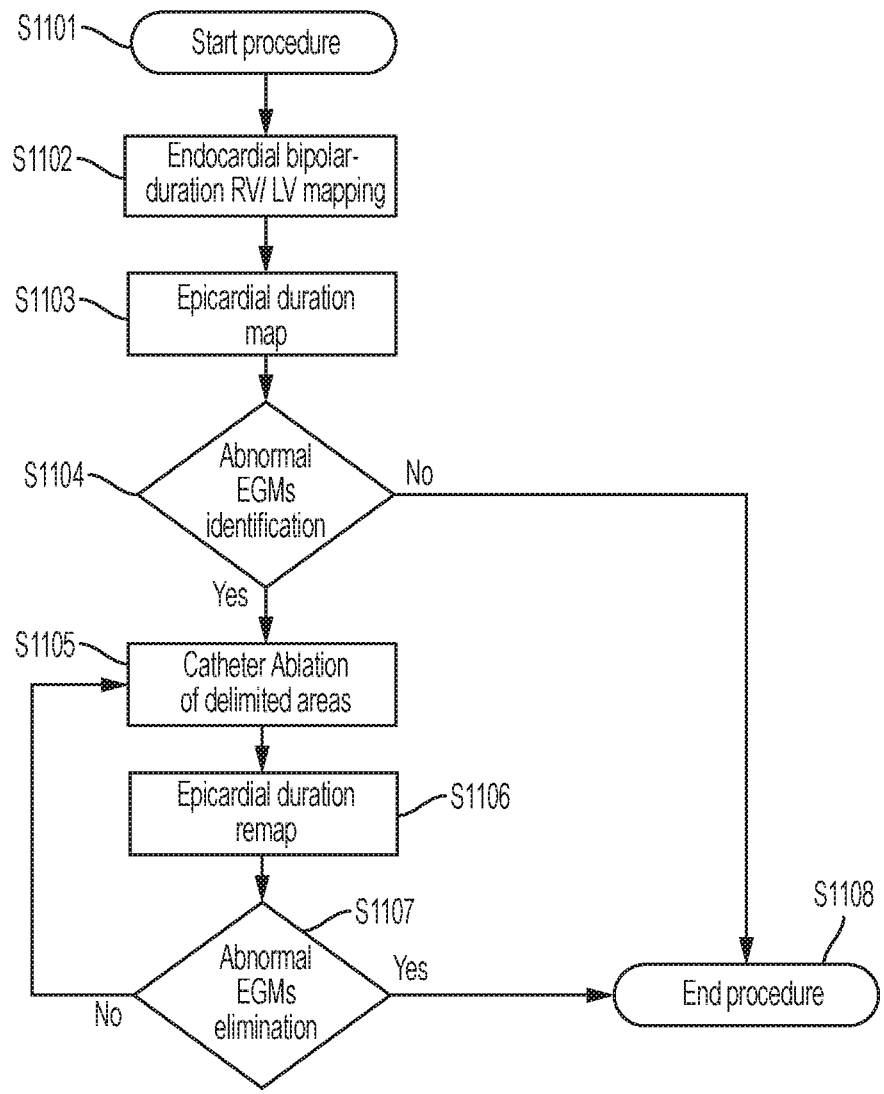
FIG. 11 shows a flow diagram of a mapping procedure in cardiomyopathies in which the inventive technique is used.

FIG. 11 is a work flow diagram showing a mapping procedure in cardiomyopathies. In step S1101, the procedure begins. This may include inserting a tool 22, such as a catheter, into a patient, and administering a drug, such as ajmaline that may be used to bring out typical findings of ST elevations in patients suspected of having Brugada syndrome.

In step S1102, endocardial bipolar-duration RV/LV mapping is performed. In one embodiment, a signal processor, e.g., computer 40, using the CFAE module of CARTO3 may be used.

In step S1103, a 3D epicardial duration map is produced. In one embodiment, this map is displayed on display 50. The epicardial duration map may comprise one or more of a voltage map, an LAT and a PDM.

In step S1104, a determination is made as to whether abnormal EGMs are identified. In one embodiment, abnormal long-duration bipolar electrograms may be defined as low-frequency (up to 100 HZ) prolonged duration (>200 ms) bipolar signals with delayed activity extending beyond the end of the QRS complex.

If abnormal EGMs are identified (S1104=YES), then in step S1105, catheter ablation of delimited areas is performed, and in step S1106, an epicardial duration remap is created. In one embodiment, catheter ablation may be performed during sinus rhythm using a stepwise strategy in a descending order of abnormal potential duration as displayed on the map and beginning from the longest potentials. In one embodiment, ablation is performed using radiofrequency (RF), which may be applied by a dragging technique that does not significantly affect either voltage amplitude or local activation times, thus immediately "homogenizing" the entire abnormal area.

In step S1107, a determination is made as to whether all abnormal EGMs have been eliminated. If all the abnormal EGMs have been eliminated (S1107=YES), then the procedure is ended at step S1108.

If no abnormal EGMs are identified (S1104=NO), then the procedure is ended at step S1108.

If not all abnormal EGMs have been eliminated (S1107=NO), that is, if one or more abnormal EGMs remain, then the procedure continues at step S1105.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It will be appreciated by persons skilled in the art, that the present invention is not limited to what has been particularly shown and described herein. Instead, the scope of the present invention includes both combinations and sub-combinations of the various features described herein, as well as variations and modifications thereof that are not in the prior art, which would occur to persons skilled in the art upon reading the foregoing description.

What is claimed is:

1. A method for identifying ablation target locations, the method comprising:
    measuring electrogram (EGM) signals;
    performing three-dimensional mapping of the EGM signals by creating a potential duration map (PDM), the PDM being created by:
        defining a window of interest (WOI) having a detected heartbeat cycle length,
        finding a potential duration start for the WOI including at least:
            (a) determining whether two consecutive peaks have a same sign and a same peak absolute value less than a predetermined threshold, (b) comparing the peak absolute value to the predetermined threshold, and (c) marking the potential duration start based at least on steps (a) and (b),
        finding a potential duration end for the WOI including at least:
            (d) comparing a duration of the two consecutive peaks to a first predetermined duration and a second predetermined duration, (e) determining whether the two consecutive peaks have the same sign and comparing the duration of the two consecutive peaks to the first predetermined duration and the second predetermined duration, and (f) marking the potential duration end based at least on steps (d) and (e),
        calculating a potential duration value as a difference between the potential duration start and the potential duration end, and
        creating the PDM based on the potential duration value; and
    identifying ablation target locations based on the PDM.

2. The method according to claim 1, the step of performing three-dimensional mapping comprising creating a color mapping.

3. A method for identifying ablation target locations, the method comprising:
    measuring electrogram (EGM) signals;
    performing three-dimensional mapping of the EGM signals by creating a potential duration map (PDM), the PDM being created by:
        defining a window of interest (WOI) having a detected heartbeat cycle length,
        finding a potential duration start for the WOI including:
            setting a current peak from a list of peaks in the WOI;
            determining whether two consecutive peaks have a same sign and a same peak absolute value less than a predetermined threshold;
            when the two consecutive peaks have the same sign and the same peak absolute value is less than the predetermined threshold, setting a second peak of the two consecutive peaks as the current peak, and obtaining a next peak after the two consecutive peaks; and
            when the two consecutive peaks do not have the same sign or the same peak absolute value is greater than or equal to the predetermined threshold, finding a start of the slope before the current peak and marking the start of the slope as the potential duration start,
        finding a potential duration end for the WOI,
        calculating a potential duration value as a difference between the potential duration start and the potential duration end, and
        creating the PDM based on the potential duration value; and
    identifying ablation target locations based on the PDM.

4. The method according to claim 3, the predetermined threshold is +/−0.05 mV.

5. A method for identifying ablation target locations, the method comprising:
    measuring electrogram (EGM) signals;
    performing three-dimensional mapping of the EGM signals by creating a potential duration map (PDM), the PDM being created by:
        defining a window of interest (WOI) having a detected heartbeat cycle length,
        finding a potential duration start for the WOI,
        finding a potential duration end for the WOI including:
            determining whether a duration of two consecutive peaks is greater than a first predetermined duration;
            when the duration of the two consecutive peaks is greater than the first predetermined duration, marking a start of the potential duration end as a first peak of the two consecutive peaks having a shorter duration;
            when the duration of the two consecutive peaks is less than or equal to the first predetermined duration and when the two consecutive peaks have the same sign and the peak absolute value is less than a predetermined threshold, or the duration between the two consecutive peaks is greater than the first predetermined duration, or the duration between the two consecutive peaks is less than a second predetermined duration, obtaining a next peak that is different from the two consecutive peaks and has a smaller duration than the two consecutive peaks; and when the duration of the two consecutive peaks is less than or equal to the first predetermined duration and when the two consecutive peaks with the same sign and the peak absolute value greater than or equal to the predetermined threshold, or the duration between the two consecutive peaks is less than or equal to the first predetermined duration, or the duration between the two consecutive peaks is greater than or equal to the second predetermined duration, finding a start of the slope after the first peak and marking the start of the slope after the first peak as the potential duration end, calculating a potential duration value as a difference between the potential duration start and the potential duration end, and creating the PDM based on the potential duration value; and identifying ablation target locations based on the PDM.

6. The method according to claim 5, the first predetermined duration is 120 ms.

7. The method according to claim 5, the second predetermined duration is 25 ms.

8. A system for identifying ablation target locations, comprising:
a catheter for measuring EGM signals;
a computer which is configured to:
measure electrogram (EGM) signals;
create a three-dimensional map of the EGM signals by creating a potential duration map (PDM), the computer being configured to create the PDM by:
defining a window of interest (WOI) having a detected heartbeat cycle length,
finding a potential duration start for the WOI including at least:
(a) determining whether two consecutive peaks have a same sign and a same peak absolute value less than a predetermined threshold, (b) comparing the peak absolute value to the predetermined threshold, and (c) marking the potential duration start based at least on steps (a) and (b),
finding a potential duration end for the WOI including at least:
(d) comparing a duration of the two consecutive peaks to a first predetermined duration and a second predetermined duration, (e) determining whether the two consecutive peaks have the same sign and comparing the duration of the two consecutive peaks to the first predetermined duration and the second predetermined duration, and (f) marking the potential duration end based at least on steps (d) and (e),
calculating a potential duration value as a difference between the potential duration start and the potential duration end, and
creating the PDM based on the potential duration value; and
identifying ablation target locations based on the PDM.

9. The system according to claim 8, the computer is further configured to:
set a current peak from a list of peaks in the WOI;
determine whether two consecutive peaks have a same sign and a same peak absolute value less than a predetermined threshold;
when the two consecutive peaks have the same sign and the same peak absolute value less than the predetermined threshold, set a second peak of the two consecutive peaks as the current peak, and obtain a next peak; and
when the two consecutive peaks do not have the same sign or the peak absolute value is greater than or equal to the predetermined threshold, find a start of the slope before the current peak and mark the start of the slope as the potential duration start.

10. The system according to claim 8, the computer is further configured to:
determine whether a duration of the two consecutive peaks is greater than a first predetermined duration;
when the duration of the two consecutive peaks is greater than the first predetermined duration, mark a start of the potential duration end as a first peak of the two consecutive peaks having a shorter duration;
when the duration of the two consecutive peaks is less than or equal to the first predetermined duration, and when the two consecutive peaks with the same sign and the peak absolute value is less than a predetermined threshold, or the duration between the two consecutive peaks is greater than the first predetermined duration, or the duration between the two consecutive peaks is less than a second predetermined duration, obtain a next peak that is different from the two consecutive peaks and has a smaller duration than the two consecutive peaks; and when the duration of the two consecutive peaks is less than or equal to the first predetermined duration and when the two consecutive peaks with the same sign and the peak absolute value is greater than or equal to the predetermined threshold, or the duration between the two consecutive peaks is less than or equal to the first predetermined duration, or the duration between the two consecutive peaks is greater than or equal to the second predetermined duration, find a start of the slope after the first peak and mark the start of the slope after the first peak as the potential duration end.

11. The system according to claim 8, further comprising a device displaying the three-dimensional map.

12. A computer software product for identifying ablation target locations, including a non-transitory computer readable storage medium in which computer program instructions are stored, which instructions, when executed by a computer, cause the computer to perform the steps of:
measuring electrogram (EGM) signals;
performing three-dimensional mapping of the EGM signals by creating a potential duration map (PDM), the PDM being created by:
defining a window of interest (WOI) having a detected heartbeat cycle length,
finding a potential duration start for the WOI including at least:
(a) determining whether two consecutive peaks have a same sign and a same peak absolute value less than a predetermined threshold, (b) comparing the peak absolute value to the predetermined threshold, and (c) marking the potential duration start based at least on steps (a) and (b), finding a potential duration end for the WOI including at least:
  (d) comparing a duration of the two consecutive peaks to a first predetermined duration and a second predetermined duration, (e) determining whether the two consecutive peaks have the same sign and comparing the duration of the two consecutive peaks to the first predetermined duration and the second predetermined duration, and (f) marking the potential duration end based at least on steps (d) and (e),
calculating a potential duration value as a difference between the potential duration start and the potential duration end, and
creating the PDM based on the potential duration value; and
identifying ablation target locations based on the PDM.

13. The computer software product according to claim 12, finding the potential duration start comprises:
setting a current peak from a list of peaks in the WOI;
determining whether two consecutive peaks have a same sign and a same peak absolute value less than a predetermined threshold;
when the two consecutive peaks have the same sign and the same peak absolute value is less than the predetermined threshold, setting a second peak of the two consecutive peaks as the current peak, and obtaining a next peak; and
when the two consecutive peaks do not have the same sign or the same peak absolute value is greater than or equal to the predetermined threshold, finding a start of the slope before the current peak and marking the start of the slope as the start potential duration.

14. The computer software product according to claim 12, finding the potential duration end comprises:
determining whether a duration of two consecutive peaks is greater than a first predetermined duration;
when the duration of the two consecutive peaks is greater than the first predetermined duration, marking a start of the potential duration end as a first peak of the two consecutive peaks having a shorter duration;
when the duration of the two consecutive peaks is less than or equal to the first predetermined duration and when the two consecutive peaks with the same sign and the peak absolute value is less than a predetermined threshold, or the duration between the two consecutive peaks is greater than the first predetermined duration, or the duration between the two consecutive peaks is less than a second predetermined duration, obtaining a next peak that is different from the two consecutive peaks and has a smaller duration than the two consecutive peaks; and
when the duration of the two consecutive peaks is less than or equal to the first predetermined duration and when the two consecutive peaks with the same sign and the peak absolute value is greater than or equal to the predetermined threshold, or the duration between the two consecutive peaks is less than or equal to the first predetermined duration, or the duration between the two consecutive peaks is greater than or equal to the second predetermined duration, finding a start of the slope after the first peak and marking the start of the slope after the first peak as the potential duration end.

* * * * *